(12) United States Patent
Desai et al.

(10) Patent No.: US 11,744,548 B2
(45) Date of Patent: *Sep. 5, 2023

(54) ULTRASHTELD DEVICES AND METHODS FOR USE IN ULTRASONIC PROCEDURES

(71) Applicant: Cal Tenn Innovation, Inc., Jackson, TN (US)

(72) Inventors: Siddharth Desai, Mission Viejo, CA (US); Jerry Jones, Jackson, TN (US)

(73) Assignee: Cal Tenn Innovation, Inc., Jackson, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/567,434

(22) Filed: Jan. 3, 2022

(65) Prior Publication Data

US 2022/0133267 A1 May 5, 2022

Related U.S. Application Data

(63) Continuation of application No. 16/249,724, filed on Jan. 16, 2019, now Pat. No. 11,213,274, which is a
(Continued)

(51) Int. Cl.
*A61B 8/00* (2006.01)
(52) U.S. Cl.
CPC .......... *A61B 8/4281* (2013.01); *A61B 8/4422* (2013.01); *A61B 8/4444* (2013.01); *A61B 8/4455* (2013.01)
(58) Field of Classification Search
CPC .... A61B 8/4272; A61B 8/4281; A61B 8/4422
See application file for complete search history.

(56) References Cited

U.S. PATENT DOCUMENTS 4,002,221 A 1/1977 Buchalter
4,459,854 A 7/1984 Richardson
(Continued)

FOREIGN PATENT DOCUMENTS

CN 102716503 10/2012
WO 2014126636 8/2014
(Continued)

OTHER PUBLICATIONS

Non-Final Office Action dated Jul. 16, 2021, issued in U.S. Appl. No. 16/249,724; 43 pages.
(Continued)

*Primary Examiner* — Amelie R Davis
(74) *Attorney, Agent, or Firm* — Fresh IP PLC; John R. Bednarz

(57) ABSTRACT

Devices and method are provided for ultrasound transmission without the need for external couplants, such as gels, which are typically used in conventional ultrasound procedures. In particular, ultrashields are provided for use with ultrasound probes, wherein the ultrashields have specialized layers to provide an uninterrupted pathway of acoustic conductance from the probe to the surface of the body throughout the procedure while introducing minimal to no attenuation of ultrasound wave transmission. In addition, combinations of ultrashields and probe covers are provided to provide additional features such as a microbial barrier.

19 Claims, 16 Drawing Sheets

Related U.S. Application Data continuation of application No. 15/476,468, filed on Mar. 31, 2017, now Pat. No. 10,206,653, which is a continuation of application No. 15/332,571, filed on Oct. 24, 2016, now Pat. No. 10,064,599.

(60) Provisional application No. 62/285,758, filed on Nov. 9, 2015.

(56) References Cited

U.S. PATENT DOCUMENTS

| | | | |
|---|---|---|---|
| 4,593,699 A | 6/1986 | Poncy | |
| 4,796,632 A | 1/1989 | Boyd | |
| 4,901,729 A | 2/1990 | Saitoh | |
| 5,207,225 A | 5/1993 | Oaks | |
| 5,259,383 A | 11/1993 | Holstein | |
| 5,482,047 A | 1/1996 | Nordgren | |
| 5,494,038 A | 2/1996 | Wang | |
| 5,522,878 A | 6/1996 | Montecalvo | |
| 5,676,159 A | 10/1997 | Navis | |
| 5,770,801 A | 6/1998 | Wang | |
| 5,782,767 A | 7/1998 | Pretlow, III | |
| 5,997,481 A | 12/1999 | Adams | |
| 6,039,694 A | 3/2000 | Larson | |
| 6,719,699 B2 | 4/2004 | Smith | |
| 10,064,599 B2 | 9/2018 | Desai | |
| 2003/0060735 A1 | 3/2003 | Coffey | |
| 2003/0233045 A1 | 12/2003 | Vaezy | |
| 2004/0064051 A1 | 4/2004 | Talish | |
| 2004/0167409 A1 | 8/2004 | Lo | |
| 2005/0101862 A1 | 5/2005 | Wilson | |
| 2005/0215901 A1 | 9/2005 | Anderson | |
| 2006/0030780 A1 | 2/2006 | Gelly | |
| 2007/0276241 A1 | 11/2007 | Park | |
| 2008/0139944 A1 | 6/2008 | Weymer | |
| 2008/0281197 A1 | 11/2008 | Wiley | |
| 2009/0054573 A1 | 2/2009 | Chivers | |
| 2010/0063396 A1* | 3/2010 | Anderson | A61B 8/462 600/459 |
| 2010/0162834 A1 | 7/2010 | Hindriks | |
| 2010/0179429 A1 | 7/2010 | Ho | |
| 2010/0234733 A1 | 9/2010 | Wahlheim | |
| 2011/0005320 A1 | 1/2011 | Gelman | |
| 2011/0077555 A1 | 3/2011 | Wing | |
| 2012/0150033 A1 | 6/2012 | Rauch | |
| 2012/0277640 A1 | 11/2012 | Lewis | |
| 2013/0116570 A1 | 5/2013 | Carson | |
| 2013/0116571 A1 | 5/2013 | Cox | |
| 2013/0144193 A1 | 6/2013 | Lewis | |
| 2014/0073899 A1* | 3/2014 | Cohrs | A61B 5/0095 600/407 |
| 2014/0163382 A1 | 6/2014 | Gubbini | |
| 2014/0180116 A1 | 6/2014 | Lindekugel | |
| 2015/0018686 A1* | 1/2015 | Berard-Andersen | A61B 8/4444 428/355 R |
| 2015/0150503 A1 | 6/2015 | Pamnani | |
| 2015/0245822 A1 | 9/2015 | Kim | |
| 2015/0305709 A1 | 10/2015 | Tomassi | |
| 2017/0128042 A1 | 5/2017 | Desai | |
| 2017/0202538 A1 | 7/2017 | Desai | |
| 2017/0276651 A1 | 9/2017 | Hall | |

FOREIGN PATENT DOCUMENTS

| | | |
|---|---|---|
| WO | 2014127235 | 8/2014 |
| WO | 2017083088 | 5/2017 |

OTHER PUBLICATIONS

Notice of Allowance and Fees Due, dated Sep. 1, 2021, issued in U.S. Appl. No. 16/249,724; 8 pages.

* cited by examiner

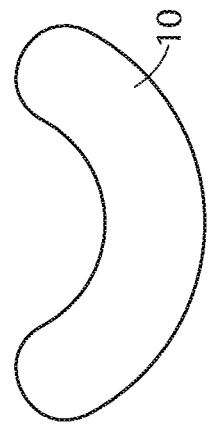
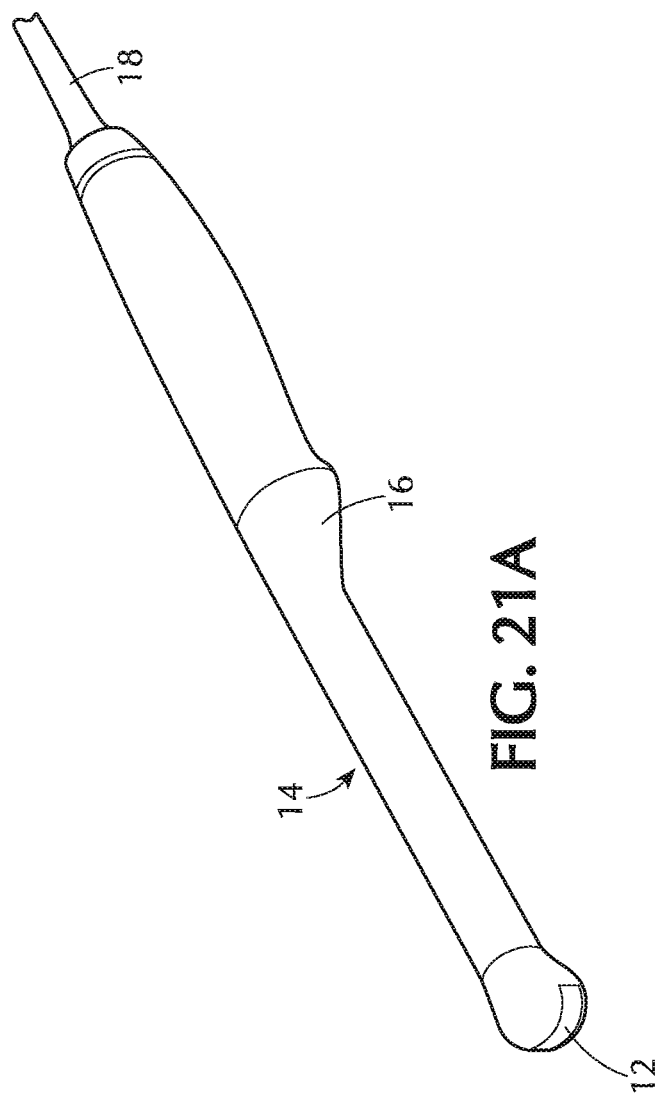

ULTRASHTELD DEVICES AND METHODS FOR USE IN ULTRASONIC PROCEDURES

CROSS-REFERENCE TO RELATED APPLICATIONS

This application is a continuation of U.S. patent application Ser. No. 16/249,724, filed Jan. 16, 2019, which is a continuation of U.S. patent application Ser. No. 15/476,468, filed Mar. 31, 2017, now U.S. Pat. No. 10,206,653, which is a continuation of U.S. patent application Ser. No. 15/332,571, filed, Oct. 24, 2016, now U.S. Pat. No. 10,064,599, which claims priority to U.S. Provisional Patent Application No. 62/285,758 entitled An Ultrasonic Couplant Design and Probe Cover Design to Replace Use of Ultrasonic Gel During Ultrasound Imaging, filed on Nov. 9, 2015, each of which are incorporated herein by reference for all purposes.

BACKGROUND OF THE INVENTION

The term "ultrasound" typically applies to acoustic energy with a frequency above human hearing (20,000 hertz or 20 kilohertz). When used in medical applications, ultrasound is typically between 1 and 30 MHz for imaging and flow measurements and between 0.05 and 1.00 MHz for therapy. The application of ultrasound in medicine began in the 1950s. It was first introduced in the field of obstetrics. Obstetric sonography is the use of medical ultrasonography in pregnancy, in which sound waves are used to create real-time visual images of the developing embryo or fetus in its mother's uterus. The procedure is a standard part of prenatal care in many countries, as it can provide a great deal of information about the health of the mother, the timing and progress of the pregnancy, and the health and development of the embryo or fetus. After that, the use of ultrasound propagated to nearly all fields of medicine including abdominal diagnostics, cardiology, urology, cerebrovascular, ophthalmology, orthopedics, breast examination, and pediatrics. Ultrasound has been proven to provide fast, accurate and safe patient imaging for an expanding array of diagnostic and therapeutic applications with ongoing technologic improvements and the growing recognition of harmful radiation from other imaging modalities.

Sonographers typically use a hand-held probe (called a transducer) that is placed directly on and moved over the patient. With the use of the probe, the sonographer is able to visualize body structures under the skin including tendons, muscles, joints, nerves, vessels and internal organs for possible pathology or lesions. Current probes utilize reflection technology. The probe transmits high-frequency ultrasound sound pulses into the body. The pulses are produced by a piezoelectric transducer within the probe. Strong, short electrical pulses from the ultrasound machine cause the crystals to change shape rapidly. The rapid shape changes, or vibrations, of the crystals produce sound waves that travel outward. The ultrasound wave travels into the body until it encounters a boundary between tissues (e.g. between fluid and soft tissue, soft tissue and bone). Some of the ultrasound waves get reflected back to the probe, while some travel on further until they reach another boundary and get reflected. The reflected waves are picked up and interpreted by the probe to produce a real-time two-dimensional representation on a monitor. Interpretation through the probe occurs when the reflected sound or pressure waves hit the piezoelectric crystals which causes them to emit electrical currents. Thus, the same crystals can be used to send and receive sound waves. The probe also has a sound absorbing substance to eliminate back reflections from the probe itself. The electric currents generated by the reflected waves are relayed to the ultrasound machine. The ultrasound machine is able to calculate the distance from the probe to the tissue or organ (boundaries) using the speed of sound in tissue (5,005 ft/s or 1,540 m/s) and the time of each echo's return (usually on the order of millionths of a second). The ultrasound machine then displays the distances and intensities of the echoes on the screen, forming a two-dimensional image. 3D images can be generated by acquiring a series of adjacent 2D images by simply moving or tilting the probe on the patient.

In order for the maximal transmission of energy from one medium to another (i.e, from the probe through the skin), the impedance of the two media should be nearly the same. Clearly, in the case of ultrasound waves passing from the probe to the tissues, this cannot be readily achieved. The greater the difference in impedance at a boundary, the greater the reflection that will occur, and therefore, the smaller the amount of energy that will be transferred. With decreased sound waves transferred, there is less energy to be reflected and interpreted by the probe. The difference in impedance is greatest for the probe/air interface which is the first one that the ultrasound has to overcome in order to reach the body. Therefore, maintaining constant and optimal contact between the probe and skin is important for the utilization of ultrasound technology. To minimize this difference, a suitable coupling medium is typically used. The coupling media used in this context includes various oils, creams and gels. The most popular is gel which is applied to the probe head and/or the body of the patient. The ultrasound coupling gel displaces air and fills contours between the piezoelectric eye, or transducer, of an ultrasound instrument (such as a probe or scanhead), which converts energy between electrical and acoustic, and the body into which the sound is being directed. Examples of ultrasound probes or scanheads can be found in U.S. Pat. No. 5,482,047 to Nordgren et al. or U.S. Pat. No. 5,207,225 to Oaks et al. This gel or fluid material, by nature of its physical and acoustic properties, serves as an ultrasound acoustic coupler between the ultrasound transducer and tissue, thereby acoustically joining the two, so that the ultrasound based information developed can freely pass back and forth between the body and the transducer.

Because of the coupling effect, this media is commonly referred to as an ultrasound couplant, ultrasound gel, scanning gel, ultrasound transmission media or acoustic transmission media. Many fluids and water-based gels have been used as ultrasound couplants over the years. Early use of mineral oil was replaced by gels whose thickness was provided from a polymer group consisting of a copolymer of methyl vinyl ether, maleic anhydride, carboxy polymethylene polymer and mixtures thereof, or from a mixture of carboxy polymethylene polymer neutralized with an alkaline agent as a primary thickener together with hydroxy alkyl cellulose as an auxiliary thickener and a polyalkylene glycol such as propylene glycol as a humectant, as described in U.S. Pat. No. 4,002,221 to Buchalter and U.S. Pat. No. 4,459,854 to Richardson et al.

Fluids and gels commonly used as ultrasound couplants have several fundamental disadvantages, some of which are described herein. To begin, patients often find the fluid or gel to be cold, sticky and messy. The fluids or gels are difficult to contain on, and remove from, the patient during and after the ultrasound procedure. Further, commercially available oils and water based gels often introduce problems to the electronics by their chemically degrading nature. They may react with the adhesives, elastomers, and epoxies used in the construction of medical ultrasound transducers, thus appreciably degrading performance and shortening their service life. With therapeutic interventions such as needle biopsies or nerve blocks, the gels may be introduced into the body which introduces additional infectious or inflammatory risks to the patient as described in further detail below.

In addition, fluids and gels offer no microbial barrier between the patient and the probe transducer; thus, latex rubber or synthetic elastomer probe covers must be applied over the probe transducer, to prevent transmission of microorganisms to the patient. Often, two layers of couplant, one inside and one outside the probe cover, are required to provide ultrasound acoustic coupling between transducer and the patient. This potential infection concern is readily apparent when the transducer is used for imaging during needle biopsy or aspiration, or inside the body during surgery in direct organ, tissue and blood contact. Of growing importance is the protection from infection by skin transmission to patients who are immune compromised by disease, organ replacement, immune system modification, chemotherapy or radiation treatments. Ultrasonic gel has been observed to have many microbial and clinical challenges as evidenced by many clinical papers. In addition, the US Food and Drug Administration has issued several warnings about microbial contaminants related to the ultrasound gel. It has also resulted in closing of a company. Furthermore, there are several papers published describing the impact of microbial issues related to the ultrasound gel.

Fluids or thickened water-based gels typically used in medical ultrasound, similarly described as in U.S. Pat. No. 4,002,221, are comprised of chemical compounds such as acrylic polymers, carboxy alkyl cellulose, hydroxyethylcellulose, carboxy polymethylene, organic acids, alkali metal salts, parabens and other germicidal and fungicidal agents, and surfactants. Such chemicals are not approved or suitable for use in applications where they may be carried into the body, such as during biopsy, intra-operative procedures, or when the transducer is placed inside a body orifice. In instances where sterile latex rubber or synthetic covers containing thickened ultrasound coupling gels are used in surgery, tearing, cutting, or rupture of the cover results in the tissue incompatible ultrasound coupling gel spilling into the body cavity. During ultrasound guided needle biopsy, aspiration, intracavity and intraoperative procedures, sterile covers produced from latex, polyurethane, polypropylene and other polymers, such as described in U.S. Pat. No. 4,593,699 to Poncy et al., U.S. Pat. No. 5,259,383 to Holstein et al. and U.S. Pat. No. 5,676,159 to Navis, are used with such tissue incompatible gel chemicals. A puncturing needle can carry such chemicals into the body, such as into the breast or into amniotic fluid, since gels are present on the skin of the patient at the point of needle insertion, as well as between the transducer and the probe cover to accomplish ultrasound acoustic coupling. Thus, as a puncturing needle passes through the gel on the skin of the patient, minute quantities of the gel may be carried into the underlying tissue and the body cavity thereby introducing a likely tissue-incompatible substance into the patient. It is apparent that this gel may also harbor bacterial organisms from manufacturing or transfer from local sources during clinical use which can then also be transferred into the body.

In addition, many practitioners also have difficulty with consistency of application. It is difficult for many practitioners to apply enough gel within a probe cover to prevent air pockets, to remain thick enough and evenly applied between the probe and cover throughout the examination without 'spilling around' edges of the probe, and without causing uneven 'wrinkles' or curvatures of the cover which causes air pockets outside the probe cover. This increases procedure time and results in suboptimal visualization of underlying structures and interferes with the quality of examination or procedure.

Therefore, improved methods and devices are desired to reliably and safely provide maximal transmission of acoustic energy during ultrasound imaging while reducing fundamental disadvantages associated with the conventional use of ultrasound couplants. At least some of these objectives will be met by the present invention.

SUMMARY OF THE INVENTION

The present invention generally relates to medical devices, systems and methods for ultrasound technology. In particular, the present invention generally relates to devices, systems and methods for creating an uninterrupted pathway of acoustic conductance from the faceplate of an ultrasonic probe to the surface of the body without externally applied couplant, such as ultrasonic gel.

In a first aspect of the present invention, a device is provided for coupling with at least a faceplate of an ultrasound probe for ultrasound transmission through a surface of a body. In some embodiments, the device comprises an ultrashield comprising a couplant layer having a couplant, and a body contact layer adjacent the couplant layer, the body contact layer having a plurality of openings which allow controlled release of the couplant from the couplant layer through the openings to the surface of the body, wherein the ultrashield provides ultrasound wave transmission from the faceplate of the ultrasound probe to the surface of the body with minimal to no attenuation. Typically, the body contact layer is configured to glide over the surface of the body with minimal friction. Thus, in some embodiments, the body contact layer comprises a material having a low coefficient of friction. In some embodiments, the body contact layer has a coefficient of friction less than or equal to natural human skin. For example, in some embodiments, the body contact layer has a coefficient of friction less than or equal to 0.5. Optionally, in some embodiments, the body contact layer has a coefficient of friction less than or equal to 0.1. Example materials include polyester, polyvinylidene fluoride or polytetrafluoroethylene.

In some embodiments, the couplant comprises water. In some embodiments, the couplant layer comprises ultrasonic gel. In some embodiments, the couplant layer comprises a hydrogel. In some embodiments, the couplant layer comprises a thermoplastic elastomer, a polymer matrix or a collagen material. In some embodiments, the couplant layer comprises a pouch filled with the couplant. In some embodiments, the couplant is selected from the group consisting of water, silicone oil, silicone gel, propylene glycol, glycerin, a corrosion inhibitor, carboxy polymethylene, cellulose, amino alcohol, a surfactant, a preservative, and combinations thereof.

In some embodiments, each opening of the plurality of openings is in the range of up to 10 microns.

In some embodiments, the body contact layer is sufficiently flexible to allow compression of the couplant layer. Optionally, the body contact layer is sufficiently stretchable to move axially so as to conform to the surface of the body as the probe glides thereover.

In some embodiments, the device further comprises a probe contact layer configured to mate with the couplant layer and adhere to the ultrasound probe. In other embodiments, the device further comprises a probe cover having at least a bottom surface configured to cover the faceplate of the ultrasound probe, wherein the ultrashield is disposed along the bottom surface so that the bottom surface and ultrashield provide ultrasound wave transmission from the faceplate of the ultrasound probe to the surface of the body with minimal to no attenuation. In some instances, the ultrashield is integral with the probe cover. In other instances, the ultrashield further comprises a probe contact layer configured to mate with the couplant layer and adhere to the bottom surface of the probe cover. Optionally, the device may further comprise a removable protective pouch extending over the ultrashield, wherein the pouch resists loss of couplant from the couplant layer.

In some embodiments, the device further comprises a replenishment mechanism configured to replenish the couplant layer with couplant. In some instances, at least a portion of the replenishment mechanism is pre-filled with couplant.

In some embodiments, the ultrashield has a thickness in the range of 0.1 to 0.3 inches, more particularly 0.110 to 0.220 inches.

It may be appreciated that the ultrashield creates an uninterrupted pathway of acoustic conductance from the faceplate of the probe to the surface of the body without externally applied couplant to the probe or the surface of the body when the probe is applied to the surface of the body for ultrasound transmission therethrough.

In a second aspect of the present invention, a probe cover is provided for encasing an ultrasound probe during ultrasound transmission through a surface of a body, such as for ultrasound imaging. In some embodiments, the probe cover comprises a bottom surface configured to cover a faceplate of the ultrasound probe; and an ultrashield disposed along the bottom surface, the ultrashield comprising a couplant layer having a couplant, and a body contact layer adjacent the couplant layer, the body contact layer having a plurality of openings which allow controlled release of the couplant from the couplant layer through the openings to the surface of the body, wherein the bottom surface and ultrashield provide ultrasound wave transmission from the faceplate of the ultrasound probe to the surface of the body with minimal to no attenuation. In some embodiments, the couplant layer comprises a hydrogel. In some embodiments, the body contact layer is configured to glide over the surface of the body with minimal friction. In some embodiments, the body contact layer comprises a material having a low coefficient of friction. In some embodiments, the body contact layer has a coefficient of friction less than or equal to natural human skin. For example, in some embodiments, the body contact layer has a coefficient of friction less than or equal to 0.5. Optionally, the body contact layer may have a coefficient of friction less than or equal to 0.1. Example materials include polyester, polyvinylidene fluoride and polytetrafluoroethylene.

In some embodiments, the couplant comprises water. In some embodiments, the couplant layer comprises a hydrogel. In some embodiments, the couplant layer comprises a thermoplastic elastomer, a polymer matrix or a collagen material. In some embodiments, the couplant layer comprises a pouch filled with the couplant. In some embodiments, the couplant is selected from the group consisting of water, silicone oil, silicone gel, propylene glycol, glycerin, a corrosion inhibitor, carboxy polymethylene, cellulose, amino alcohol, a surfactant, a preservative, and combinations thereof.

In some embodiments, each opening of the plurality of openings is in the range of up to 10 microns.

In some embodiments, the body contact layer is sufficiently flexible to allow compression of the couplant layer. Optionally, the body contact layer is sufficiently stretchable to move axially so as to conform to the surface of the body as the probe glides thereover.

In some embodiments, the ultrashield further comprises a probe contact layer configured to mate with the couplant layer and adhere to the probe cover. In other embodiments, the ultrashield is integral with the probe cover. Optionally, the probe cover may further comprise a removable protective pouch extending over the ultrashield, wherein the pouch resists loss of couplant from the couplant layer.

In some embodiments, the probe cover further comprises a replenishment mechanism configured to replenish the couplant layer with couplant. In some instances, at least a portion of the replenishment mechanism is pre-filled with couplant.

In some embodiments, the ultrashield has a thickness in the range of 0.1 to 0.3 inches, more particularly 0.110 to 0.220 inches.

It may be appreciated that the probe cover creates an uninterrupted pathway of acoustic conductance from the faceplate of the probe to the surface of the body without externally applied couplant to the probe or the probe cover when the probe is applied to the surface of the body for ultrasound transmission therethrough.

In another aspect of the present invention, a method of transmitting ultrasound through a surface of a body with an ultrasound probe is provided. In some embodiments, the method comprises covering a faceplate of the ultrasound probe with an ultrashield, wherein the ultrashield comprises a couplant layer having a couplant, and a body contact layer adjacent the couplant layer, the body contact layer having a plurality of openings which allow controlled release of the couplant from the couplant layer through the openings to the surface of the body. Such methods further include contacting the ultrashield to the surface of the body so that the ultrashield creates an uninterrupted pathway of acoustic conductance from the faceplate of the probe to the surface of the body without externally applied couplant to the probe or the surface of the body, and transmitting ultrasound through the surface of the body with the faceplate of the ultrasound probe.

In some embodiments, when the ultrashield comprises a probe contact layer adjacent to the couplant layer, covering the faceplate comprises adhering the probe contact layer to the faceplate of the ultrasound probe. In some embodiments, the ultrashield is carried by a probe cover, and covering the faceplate comprises covering the faceplate with the probe cover so that the ultrashield covers the faceplate of the ultrasound probe.

In some embodiments, the ultrashield is covered by a protective pouch and the method further comprising removing the protective pouch prior to contacting the ultrashield to the surface of the body. In some instances, the method further comprises replenishing the couplant. Optionally, replenishing the couplant comprises activating a replenishment system.

It may be appreciated that in some embodiments, transmitting ultrasound comprises imaging through the surface of the body.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 21A-21B illustrate an example probe having a smaller curved faceplate and an ultrashield having a corresponding shape.

DETAILED DESCRIPTION OF THE INVENTION

Specific embodiments of the disclosed devices and methods will now be described with reference to the drawings.

Figure 1:
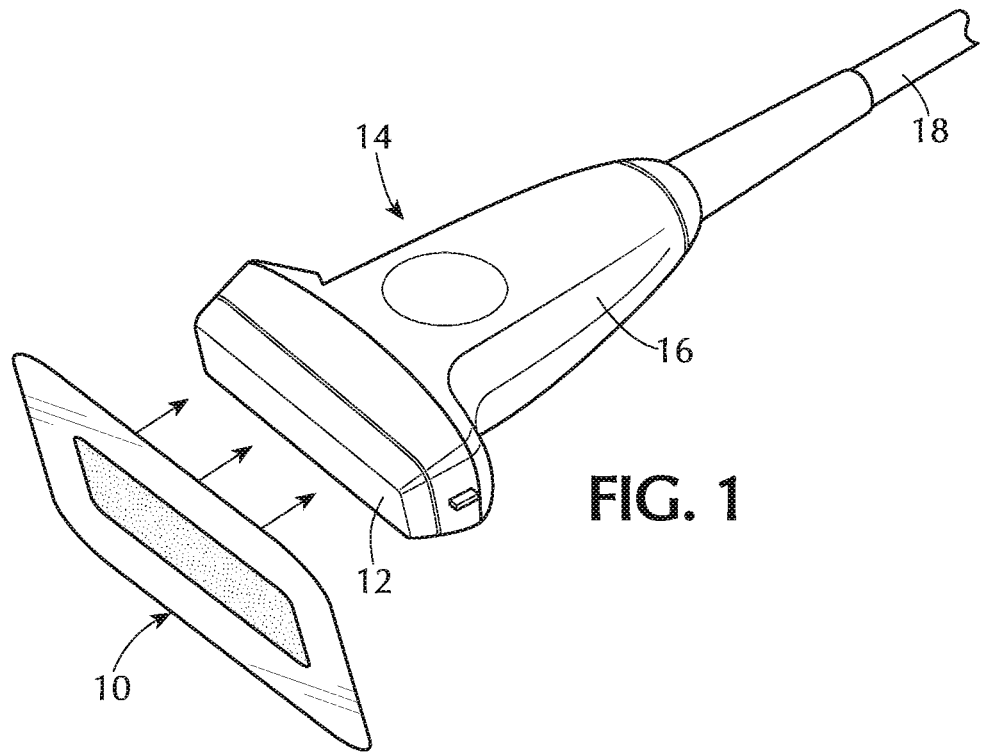
FIG. 1 illustrates an embodiment of an ultrashield and a probe to which the ultrashield is affixable.
Figure 2:
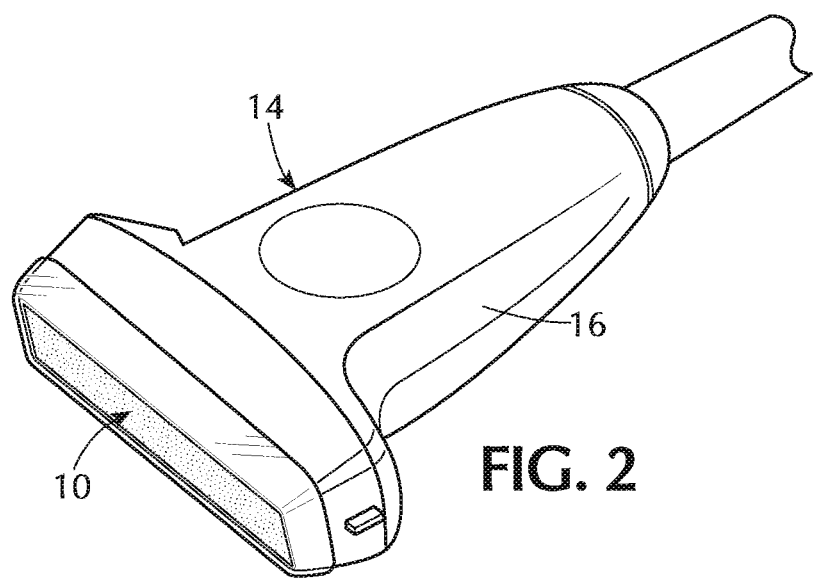
FIG. 2 illustrates an ultrashield sized and configured so that portions of its exterior edge wrap around the probe.

Devices and methods are provided for specific use with ultrasound machines to enable a clinician or a technician to use a conventional ultrasound probe, such as to generate an ultrasonic image, without the need for external ultrasonic gel or similar couplant. In particular, an ultrashield is provided for use with a conventional ultrasound probe that eliminates the need for additional ultrasonic couplants, such as gels. The ultrashield is a cover or shield which is positioned over the faceplate of an ultrasound probe, either alone or in conjunction with a probe cover. FIG. 1 illustrates an embodiment of an ultrashield 10 which is sized and configured to affix to the faceplate 12 of an ultrasound probe 14, as indicated by arrows. Typically, the ultrashield 10 is sized and configured so that portions of its exterior edge wrap around the probe 14, beyond the faceplate 12, so as to ensure a complete seal, as illustrated in FIG. 2. The ultrasound probe 14 comprises a housing 16 which contains the piezoelectric crystal, electrodes, and acoustic insulator. The housing 16 is connected with a coaxial cable 18 which extends to the ultrasound machine (not shown). The ultrasound waves are transmitted from the piezoelectric crystal through the faceplate 12, to the body of the patient. By affixing the ultrashield 10 to the faceplate 12, the ultrasound waves pass directly through the ultrashield 10, without introducing an air barrier or a significant difference in impedance. Likewise, when the probe 14 is in use, the ultrashield 10 contacts the surface of the patient, again without introducing a barrier or a significant difference in impedance. Particular features of the ultrashield 10 allow its use without a traditional external gel couplant as will be described herein.

Figure 3A:
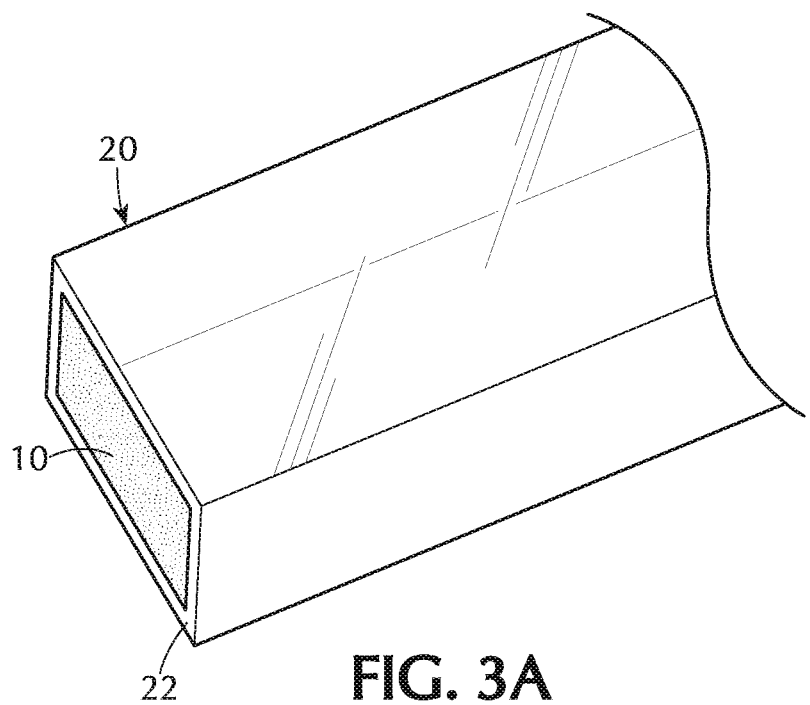
FIGS. 3A-3B illustrate an embodiment of a probe cover having an ultrashield.
Figure 3B:
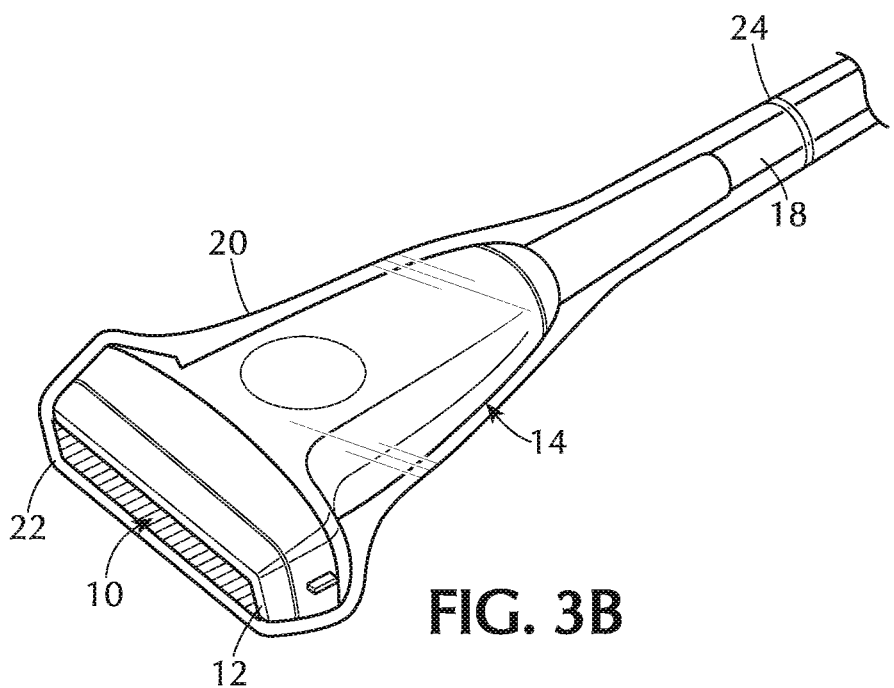

FIGS. 3A-3B illustrate an embodiment of a probe cover 20 having an ultrashield 10. Such a probe cover 20 is typically used in sterile conditions in an operating room. The probe cover 20 allows the use of the probe 14 in scanning and needle guided procedures for body surface, endocavity and intra-operative diagnostic ultrasound procedures, while helping to prevent transfer of microorganisms, body fluids and particulate material to the patient and healthcare worker during reuse of the probe 14. The probe cover 20 provides an extremely important need which is to provide a removable barrier between the probe 14 and the individual patient which will prevent infectious particles from being transmitted to different patients due to inadequate cleanings of the probe between uses. Such a barrier between the patient and the probe 14 (that is exchanged between probe uses) is particularly important for many probes 14 which have crevices and contours that have been found to be very difficult to definitively clean, leading to an increased risk of spreading infectious particles.

In this embodiment, the probe cover 20 has an oblong, rectangular shape, as illustrated in FIG. 3A, with a bottom surface 22 having a rectangular shape for use with a probe having a rectangular shaped faceplate 12. However, it may be appreciated that such probe covers 20 may have various shapes and forms for accommodating various types of probes. In this embodiment, the ultrashield 10 is disposed along the bottom surface 22. The cover 20 is then positioned over the probe 20. FIG. 3B illustrates the probe cover 20 of FIG. 3A positioned on a probe 14. Here, the ultrashield 10 is aligned with the faceplate 12 of the probe 14 and the cover 20 is pulled up tightly around the probe, so as to remove any wrinkles, taking care to avoid puncturing the cover. The cover 20 may be secured to the cable 18 with bands 24. The use of such a specialized probe cover 20 eliminates the need for application of a gel couplant inside the cover and/or on the faceplate. This saves preparation time, reduces damage to the probe, eliminates the possibility of puncture and leakage of gel, reduces clean up time and eliminates the possibility of cross-contamination due to gel residue trapped in the probe 14.

Figure 4:
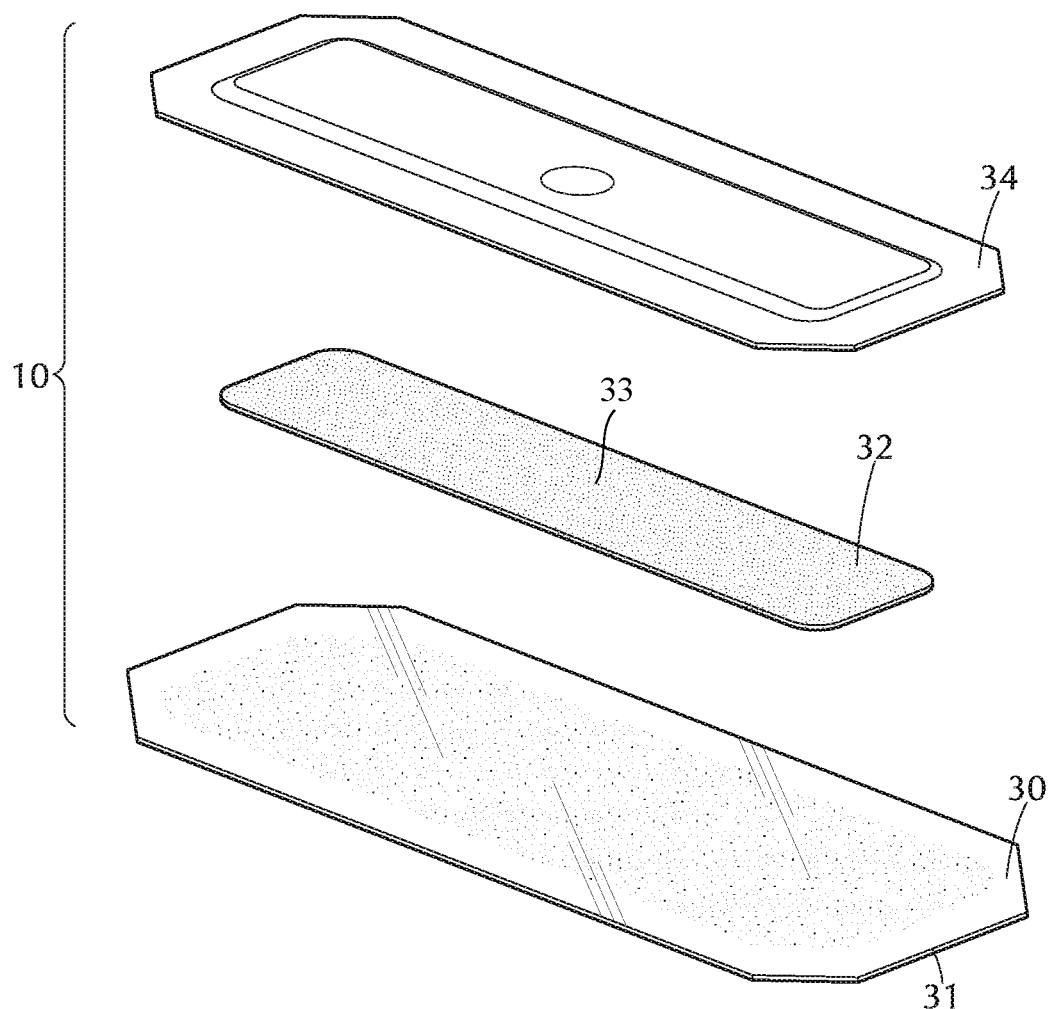
FIG. 4 illustrates an embodiment of an ultrashield in an expanded view.
Figure 5:
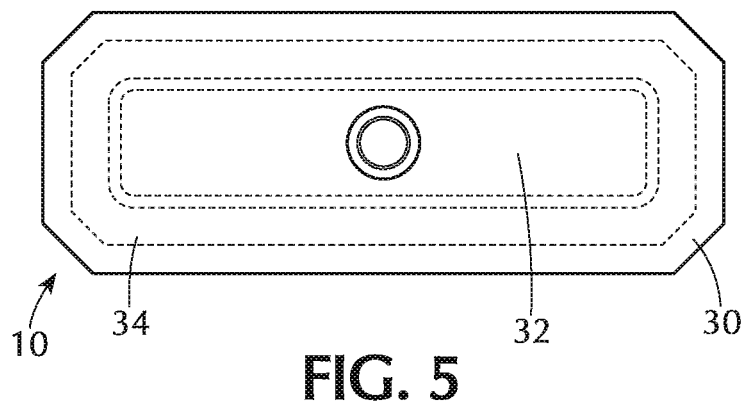
FIG. 5 illustrates the ultrashield embodiment of FIG. 4 in an unexpanded view.

As mentioned, when the clinician starts ultrasonic imaging, the probe 14 is able to visualize through the ultrashield 10 and it moves along with the probe 14. The separate gel couplant is not required due to the specialized properties of the ultrashield 10 that provide ultrasonic conductivity along with ease of gliding over the patient skin or body surface. Such specialized properties are provided by various layers that make up the ultrashield 10. These layers are also echogenic and facilitate transmission of ultrasonic waves with minimal or no loss. FIG. 4 illustrates an embodiment of an ultrashield 10 in an expanded view revealing various layers. In this embodiment, the layers include a probe contact layer 30, an intermediate sandwich layer or couplant layer 32, and an outer surface body contact layer 34. These layers will be described in more detail below. FIG. 5 illustrates the ultrashield 10 embodiment of FIG. 4 in an unexpanded view wherein the layers 30, 32, 34 are stacked and adhered together to form a single multi-layered sheet. As shown, the ultrashield 10 has a thin, compact design which is easily packaged, handled and applied to the head of a probe 14. It may be appreciated that the ultrashield 10 may take a variety of forms. In some embodiments, the ultrashield 10 includes all of the layers depicted in FIGS. 4-5, however the invention is not so limited. For example, in some embodiments, aspects of a particular layer are provided by another layer of the ultrashield 10 or the probe cover 20.

Probe Contact Layer

The probe contact layer 30 provides an integrated polymeric surface that connects with the probe 14 and gives a connection that is substantially free of any air or vacuum. This ensures that the ultrashield 10 will be integral to the probe 14 as a 'seamless' surface. The probe contact layer 30 is typically comprised of a flexible film, such as flexible polymer film. In some embodiments, the film includes a rigid layer, such as a rigid center layer, to provide additional structure. The central rigid layer typically resides along the portion of the probe contact layer 30 that covers the faceplate 12 of the probe 14, allowing a more flexible portion of the contact layer 30 (such as disposed around the rigid center layer) to bend around the probe 14.

In some embodiments, the contact layer 30 has a thickness in the range of 0.010 to 0.060 inches, more particularly 0.030 to 0.060 inches. Similarly, in some embodiments, the contact layer 30 has a thickness of less than or equal to 0.060 inches, less than or equal to 0.050 inches, less than or equal to 0.040 inches, or less than or equal to 0.020 inches. In some embodiments, the contact layer 30 is comprised of quartz or a polymer such as polyethylene, polyurethane, polypropylene, polyester, ethylene vinyl acetate, polyvinyl chloride, or the like. In each of these instances, the layer 30 has a low level of attenuation co-efficient and shall provide minimal or no diminishment of ultrasound wave transmission.

Typically, the probe contact layer 30 includes an adhesive 31 on at least one side of the contact layer 30. The adhesive 31 allows the ultrashield 10 to be affixed to the probe 14, such as the faceplate 12 of the probe 14 and optionally the housing 16. This creates an airless connection between the ultrashield 10 and the probe 14. In some embodiments, the probe contact layer 30 includes an adhesive 31 to adhere the couplant layer 32 and/or the outer surface body contact layer 34 thereto.

Typically, the adhesive 31 has a very fine thickness, such as 0.001 to 0.005 inches, more particularly 0.002 to 0.003 inches. Example adhesives 31 include epoxy, polyurethane, cyanoacrylate and acrylic polymers, to name a few. In some embodiments, the adhesive 31 comprises a pressure adhesive wherein upon application of pressure the contact layer 30 adheres to the probe 14 and when it is pulled for removal it leaves behind negligible or no residue. It may be appreciated that the adhesive 31 shall provide minimal or no diminishment of ultrasound wave transmission as well.

Couplant Layer

In this embodiment, the couplant layer 32 comprises a couplant material 33 such as a hydrogel, collagen material, polymer matrix and/or thermoplastic elastomer containing a couplant. The couplant material 33 has a very low acoustic attenuation coefficient, such as 0.05 dB/cm/MHz or less at a frequency of 1540 MHz (human tissue), so that it transmits the ultrasonic wave with minimal to no loss of energy. The lower the attenuation coefficient, the better is the transmission of ultrasonic wave through the material. In preferred embodiments, the couplant within the couplant material 33 comprises water which has the lowest attenuation coefficient. However, other couplants may be used such as glycerin, silicone oil, silicone gel or other ultrasound gels, such that have very low attenuation coefficients. The couplant layer 32 typically has a thickness in the range of approximately 0.060 to 0.150 inches, more particularly 0.010 to 0.040 inches. Likewise, the couplant layer 32 is typically flexible or pliable by means of a low durometer profile, such as a durometer between 10-20 Shore A-2.

In some embodiments, the couplant material 33 is comprised of a hydrogel material which retains water in a colloidal condition for extended periods of time. Hydrogels are polymer networks extensively swollen with water. Hydrogels are made of crosslinked water-soluble polymers. Because of the crosslinks, hydrogels can absorb water and get swollen, but cannot be dissolved. In particular, the ability of hydrogels to absorb water arises from hydrophilic functional groups attached to the polymeric backbone, while their resistance to dissolution arises from cross-links between network chains. Through many intricate customizations, a hydrogel can be sensitive or responsive to the fluctuations in its external environment, such as, temperature, pH, ionic strength, electric stimulus, etc Hydrogels inherently possess a degree of flexibility very similar to natural tissue due to their large water content. Such flexibility, along with the ability to be formed into sheets and the ability to retain water, make hydrogels a desired couplant layer 32.

In some instances, the couplant layer 32 is inherently adhesive. For example, couplant materials 33 having greater than 95% water are typically self-adhesive. In such instances, the layer 32 may adhere to the probe contact layer 30 and/or outer surface body contact layer 34 without additional adhesives 31.

Figure 6:
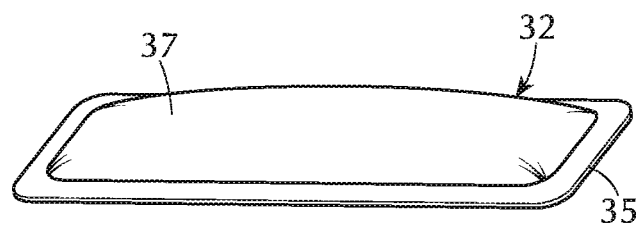
FIG. 6 illustrates an embodiment of a couplant layer comprising a couplant pouch.

In other embodiments, the couplant layer 32 comprises a couplant pouch 35 containing a couplant 37, as illustrated in FIG. 6. In such embodiments, the couplant pouch 35 has similar dimensions or volume as a couplant material 33 with a thickness of approximately 0.030 inches (30 mil) for fill volume. The probe contact layer 30 is typically comprised of a flexible polymer such as polyethylene, polyurethane, polypropylene, polyester, ethylene vinyl acetate, polyvinyl chloride, or the like. In each of these instances, the pouch 35 has a low level of attenuation co-efficient and shall provide minimal or no diminishment of ultrasound wave transmission.

The couplant pouch 35 is filled with one or more couplants 37 and/or other materials, such as preservatives or additives. For example, in some embodiments the couplant pouch 35 is filled with one or more of the following:

Water (such as 7732-18-5)
Silicone oil
Silicone gel
Propylene Glycol (such as 57-55-6)
Ultrasound gel
Glycerin (such as 56-81-5)
Corrosion Inhibitors
Carboxy Polymethylene (such as 9003-01-4)
Cellulose (such as 9004-62-0)
Amino Alcohol
Surfactant
Preservative (such as 78491-02-8)

It may be appreciated that in some embodiments, the couplant layer 32 is comprised of conventional ultrasound gel or lotion. Thus, in some embodiments, the couplant layer 32 is comprised of a thin layer of conventional ultrasound gel itself. Alternatively, in other embodiments, the couplant layer 32 is comprised of a couplant material 33 which includes conventional ultrasound gel or lotion, or the couplant layer 32 is comprised of a couplant pouch 35 which includes conventional ultrasound gel or lotion.

In each of the embodiments described herein, the couplant layer 32 is selected for its favorable ultrasonic wave transmission ability. Since the layer 32 does not come in direct contact with the tissue or skin of the patient, the choice of couplant layer 32, material 33 or pouch 35 is not limited by other parameters, such as wearability, coefficient of friction, or adhesion. Therefore, the couplant layer 32, material 33 or pouch 35 providing superior ultrasonic transmission ability may be used. Likewise, in each of these embodiments, the couplant layer 32 forms an air pocket-free layer to provide superior ultrasonic without the need for additional external couplants such as conventional gels.

Outer Surface Body Contact Layer

The outer surface body contact layer 34 is configured to glide easily over the tissue or skin of the patient's body against which it is in contact. Thus, the body contact layer 34 is the outermost surface of the probe 14 when the ultrashield 10 is mounted thereon. Such glide-ability is due to various characteristics of the layer 34. To begin, in some embodiments, the body contact layer 34 is comprised of a material having a low coefficient of friction. The coefficient of friction is the ratio between the force of sliding friction and the normal force. In some embodiments, the body contact layer 34 has a coefficient of friction that is less than or equal to the coefficient of friction of natural human skin, such as dry skin unwetted by emollients, lotions or petrolatums. The coefficient of friction for natural skin various across the human body. The palm of the hand has the highest coefficient of friction on the body, in the range of approximately 0.4-0.84 (0.62+/−0.22). However, the average coefficient of friction for natural skin is in the range of approximately 0.31-0.61 (0.46+/−0.15). Thus, in some embodiments, the body contact layer 34 has a coefficient of friction that is less than or equal to the coefficient of friction of the palm of the hand (less than 0.84, less than 0.62 or less than 0.4, to name a few). Likewise, in some embodiments, the body contact layer 34 has a coefficient of friction that is less than the average coefficient of friction of natural skin (less than 0.61, less than 0.046 or less than 0.31, to name a few). Thus, in some embodiments, the body contact layer 34 has a coefficient of friction of less than or equal to 0.5. In preferred embodiments, the body contact layer 34 has a coefficient of friction that is less than or equal to 0.1.

This is in contrast to a typical hydrogel which alone typically has a coefficient of friction that is greater than 1. In some embodiments, the body contact layer 34 is comprised of a film having a low coefficient of friction, such as polyester, polyvinylidene fluoride (PVDF) and polytetrafluoroethylene (PTFE) or TEFLON™. It may be appreciated that in some embodiments, the contact layer 34 is plasma treated or coated with a fine film of biocompatible material to reduce friction. In some embodiments, the body contact layer 34 has a thickness in the range of approximately 0.010 to 0.070 inches, more particularly 0.020 to 0.060 inches.

The outer surface body contact layer 34 has controlled openings, such as submicron or micron sized openings (e.g. 1 nm, 0.05 µm to 2.0 µm), which both assist in retention of couplant within the adjacent couplant layer 32 and allow a slow release of the couplant from the couplant layer 32 to the skin or body surface. Thus, the body contact layer 34 can be considered as a filter itself or it may be comprised of such a filter. In such embodiments, the body contact layer 34 may comprise openings of uniform or varying sizes, including 0.2-2.0 micron, 0.5-5 micron, 1 micron, 2 micron, 3 micron, 4 micron, 5, micron, up to 10 micron, 10 micron, to name a few. The release of couplant creates an uninterrupted pathway of acoustic conductance from the probe 14 to the skin or body surface of the patient. In other words, the release of couplant to the body surface causes the body surface to be acoustically conductive with the ultrasound. In many instances, the couplant is water which is non-obtrusive to the patient and easily absorbed, evaporated or wiped away after the procedure. Likewise, the body contact layer 34 is typically hydrophilic so as to be acoustically conductive as well.

In some embodiments, the body contact layer 34 creates a stretchable surface that moves axially as the probe 14 is moved over the tissue or skin of the patient so as to mimic the conventional gel function without compromising the body contact layer 34 and the body interface. In some embodiments, the body contact layer 34 is comprised of a membrane with at least 50% elongation to allow the probe 14 to adhere to the skin of body surface.

In some embodiments, the body contact layer 34 is sufficiently flexible so as to allow the compression of the sandwich layer 32. It may be appreciated that many liquids, such as water, are essentially incompressible. Therefore, when the sandwich layer 32 includes one or more liquids, the contact layer 34 is expandable to allow for shifting of the liquid due to compression of the sandwich layer 32 by the probe 14.

In some embodiments, the body contact layer 34 creates a breathing surface so that any potential air trapped between the skin and the contact layer 34 is moved away from the contact layer 34. In some instances, couplant, such as water, exiting the body contact layer 34 pushes any trapped air outward, creating a continuous ultrasonic connection.

It may be appreciated that although the body contact layer 34 controls elution of couplant from the couplant layer 32, resisting quick emptying, it is possible for the couplant to eventually empty. In such instances, the couplant layer 32 may be re-filled with couplant through the body contact layer 34. For example, the body contact layer 34 may be placed into couplant to allow the couplant to absorb through the controlled openings of the layer 34 and into the couplant layer 32 for replenishment.

It may be appreciated that if the couplant layer 32 was in direct contact with the patient's skin, it would be very difficult to glide. Hydrogels and other polymer matrices are characteristically sticky and therefore do not glide easily if at all over skin or various body surfaces. The couplant layer 32 alone would also flow the couplant out onto the patient's skin without any control and may dispense all the couplant immediately, thereby rendering its effectiveness to be for a very short duration.

In some embodiments, the couplant layer 32 comprises a couplant material 33 having a rectangular shape, such as approximately 2.5 inches (63.50 mm) long and 0.5 inches (12.70 mm) wide, and an adhesive sheet 35 having a larger rectangular shape, such as approximately 3.25 inches (82.55 mm) long and 1.25 inches (31.75 mm) wide. In some embodiments, the body contact layer 34 also has a rectangular shape, such as approximately 3 inches (76.20 mm) long and 1.0 inch (25.40 mm) wide. In some embodiments, the probe contact layer 30 also has a rectangular shape, such as approximately 3.39 inches (86 mm) long and 1.38 inches (35 mm) wide. It may be appreciated that such dimensions are exemplary for a conventional probe having a rectangular faceplate. Ultrashields having other dimensions may be used, particularly for other shaped probes.

Figure 7:
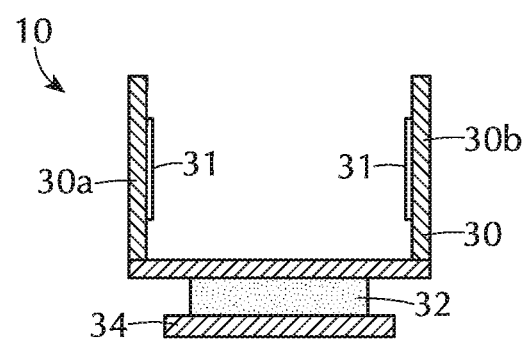
FIGS. 7-8 schematically illustrate an embodiment of an ultrashield wherein the couplant layer comprises a couplant material.
Figure 8:
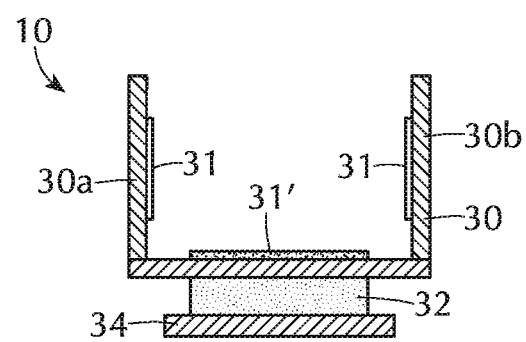

FIG. 7 schematically illustrates an embodiment of an ultrashield 10. In this embodiment, the ultrashield 10 comprises a probe contact layer 30, an couplant layer 32 and an outer surface body contact layer 34. In this illustration, the body contact layer 34 is shown curving upwards so as to affix to a probe 14 as previously illustrated in FIG. 2. Thus, in this embodiment, the probe contact layer 30 is configured to extend further along the probe 14 than simply along the faceplate 12. In this embodiment, portions of the probe contact layer 30 form side walls 30a, 30b which are configured to extend up and along the housing 16 of the probe 14. Thus, in some embodiments the probe contact layer 30 includes adhesive 31 along the inner surface of the side walls 30a, 30b so as to adhere the side walls 30a, 30b, and therefore the ultrashield 10, to the probe 14. In this embodiment, the ultrashield 10 further includes an couplant layer 32 comprising a couplant material 33. Likewise, this embodiment includes a body surface layer 34 configured to contact the patient's skin. The body surface layer 34 controls the amount and rate of liquid couplant dispensed. Since the body surface layer 34 has a low co-efficient of friction, it glides easily on the patient skin. Referring to FIG. 8, in some embodiments, the ultrashield 10 also includes an adhesive 31' disposed along the probe contact layer 30 at a location so as to adhere the probe contact layer 30 to the faceplate 12 of the probe 14. It may be appreciated that the adhesive 31, 31' may cover a variety of surfaces of the probe contact layer 30, including all surfaces of the probe contact layer 30, to assist in adhering the ultrashield 10 to the probe 14.

Figure 9:
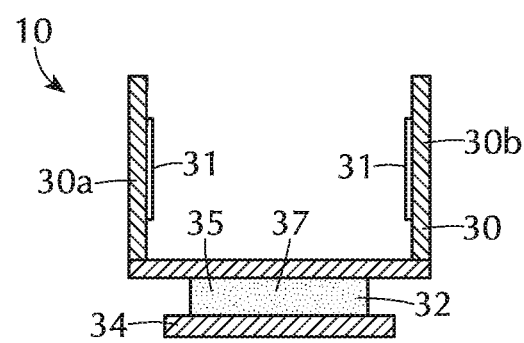
FIGS. 9-10 schematically illustrate an embodiment of an ultrashield wherein the couplant layer comprises a couplant pouch.
Figure 10:
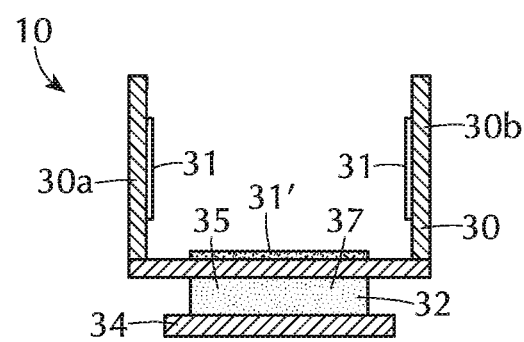

FIG. 9 schematically illustrates another embodiment of an ultrashield 10. In this embodiment, the probe contact layer 30 also has side walls 30a, 30b which are configured to extend up and along the housing 16 of the probe 14. Thus, the probe contact layer 30 includes adhesive 31 at least along the inner surface of the side walls 30a, 30b so as to adhere the side walls 30a, 30b, and therefore the ultrashield 10, to the probe 14. In this embodiment, the ultrashield 10 further includes an couplant layer 32 comprising a couplant pouch 35 containing a couplant 37, such as water or glycerin. Likewise, this embodiment includes a body surface layer 34 configured to contact the patient's skin. Again, the body surface layer 34 controls the amount of and rate of liquid couplant 37 release. Since the body surface layer 34 has a low co-efficient of friction, it glides easily on the patient skin. Referring to FIG. 10, in some embodiments, the ultrashield 10 also includes an adhesive 31' disposed along the probe contact layer 30 at a location so as to adhere the probe contact layer 30 to the faceplate 12 of the probe 14. It may be appreciated that the adhesive 31, 31' may cover a variety of surfaces of the probe contact layer 30, including all surfaces of the probe contact layer 30, to assist in adhering the ultrashield 10 to the probe 14.

Figure 11:
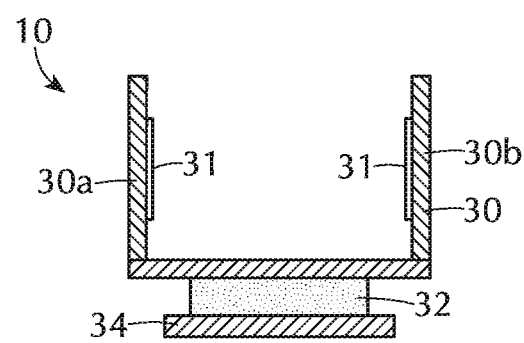
FIG. 11 schematically illustrates an embodiment of an ultrashield wherein the couplant layer comprises a thermoplastic elastomer.

FIG. 11 schematically illustrates another embodiment of an ultrashield 10. In this embodiment, the probe contact layer 30 again has portions acting as side walls 30a, 30b which are configured to extend up and along the housing 16 of the probe 14. Thus, the probe contact layer 30 includes adhesive 31 along the inner surface of the side walls 30a, 30b so as to adhere the side walls 30a, 30b, and therefore the ultrashield 10, to the probe 14. In this embodiment, the ultrashield 10 further includes an couplant layer 32 comprising a thermoplastic elastomer having a couplant. Likewise, this embodiment includes a body surface layer 34 configured to contact the patient's skin. Again, the body surface layer 34 controls the amount and rate of liquid couplant dispensed. Since the body surface layer 34 has a low co-efficient of friction, it glides easily on the patient skin.

Figure 12:
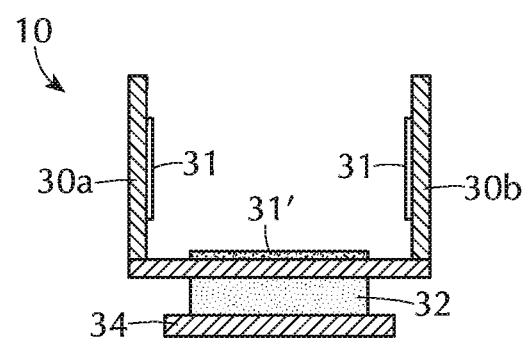
FIG. 12 schematically illustrates an embodiment of an ultrashield wherein the probe contact layer has a window through which the couplant layer extends.

FIG. 12 schematically illustrates another embodiment of an ultrashield 10. In this embodiment, the probe contact layer 30 again has portions acting as side walls 30a, 30b which are configured to extend up and along the housing 16 of the probe 14. Thus, in this embodiment, the probe contact layer 30 includes adhesive 31 at least along the inner surface of the side walls 30a, 30b so as to adhere the side walls 30a, 30b, and therefore the ultrashield 10, to the probe 14. In this embodiment, the probe contact layer 30 has a window wherein a portion of the contact layer 30 is replaced with the couplant layer 32. Thus, the couplant layer 32 is disposed so as to directly contact the faceplate 12 of the probe 14 when the ultrashield 10 is positioned thereon. To ensure adequate adhesion of the couplant layer 32 to the probe 14, particularly the faceplate 12, an adhesive 31' is disposed along the couplant layer 32 to desirably adhere the couplant layer 32 to the faceplate 12. As shown, the body surface layer 34 configured to adhere to the couplant layer 32 and the probe contact layer 30. Again, the body surface layer 34 also controls the amount and rate of liquid couplant dispensed to the patient's skin. Since the body surface layer 34 has a low co-efficient of friction, it glides easily on the patient skin.

As mentioned previously in relation to FIGS. 3A-3B, in some embodiments the ultrashield 10 is integral with a probe cover 20. The probe cover 20 provides a removable barrier between the probe 14 and the individual patient which will prevent infectious particles from being transmitted to different patients due to inadequate cleanings of the probe between uses. As mentioned, such a barrier between the patient and the probe 14 (that is exchanged between probe uses) is particularly important for many probes 14 which have crevices and contours that have been found to be very difficult to definitively clean, leading to an increased risk of spreading infectious particles.

Figure 13:
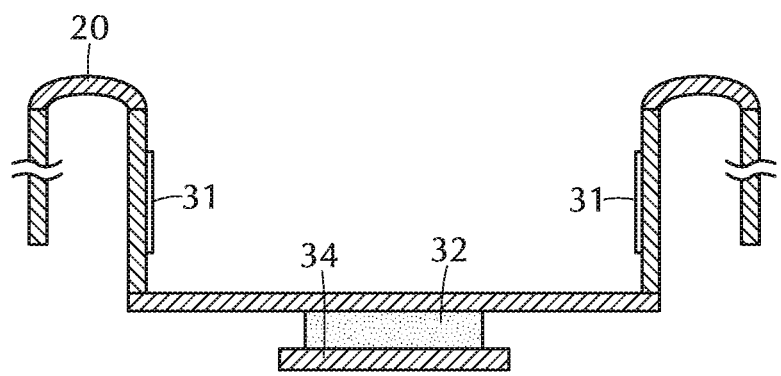
FIGS. 13-14 schematic illustrate embodiments of a probe cover having an ultrashield.
Figure 14:
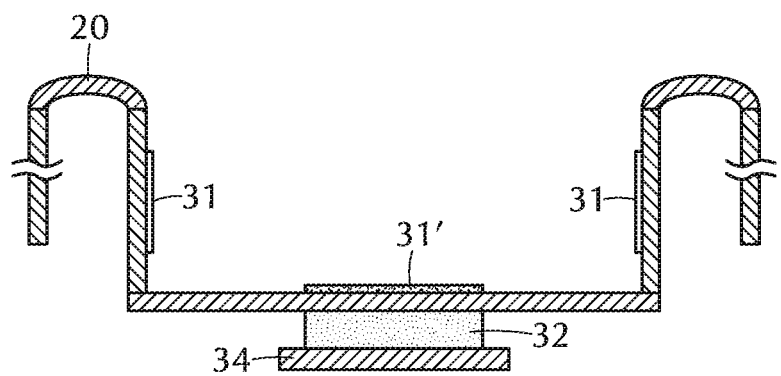

FIG. 13 is a schematic illustration of an embodiment of a probe cover 20 having an ultrashield 10. In this embodiment, the ultrashield 10 comprises an couplant layer 32 and a body surface layer 34 which are built into a bottom portion or surface of the probe cover 20. In this embodiment, the couplant layer 32 comprises a hydrogel which captures the couplant. The skin contact layer 34 comprises a filtration membrane that controls the amount and rate of liquid being delivered. It also has low co-efficient of friction and glides easily on the patient skin. It may be appreciated that in this embodiment, couplant layer 32 is directly adjacent the probe cover 20, wherein a separate probe contact layer 30 is not present. As such the probe cover 20 acts as the probe contact layer 30. The probe cover 20 is configured to extend over a probe 14 so that the ultrashield 10 is aligned with the faceplate 12 of the probe 14. Typically, the probe cover 20 includes adhesive 31 along a portion of its inner walls or surfaces to hold the cover 20 snugly to the probe 14. Referring to FIG. 14, in some embodiments, the probe cover 20 also includes an adhesive 31' disposed along the inside of the probe cover 20 at a location so as to adhere the probe cover 20 directly to the faceplate 12 of the probe 14. It may be appreciated that the adhesive 31, 31' may cover a variety of surfaces of the probe cover 20 to assist in adhering the ultrashield 10 to the probe 14.

It may be appreciated that in some embodiments the ultrashield 10 is separate from the probe cover 20 and can be adhered to a surface of the probe cover 20 for use. Thus, rather than adhering the probe contact layer 30 directly to the probe 14, the probe contact layer 30 is adhered to the probe cover 20. This allows the user to utilize the ultrashield 10 with any probe cover 20 or similar device.

Packaging

Figure 15:
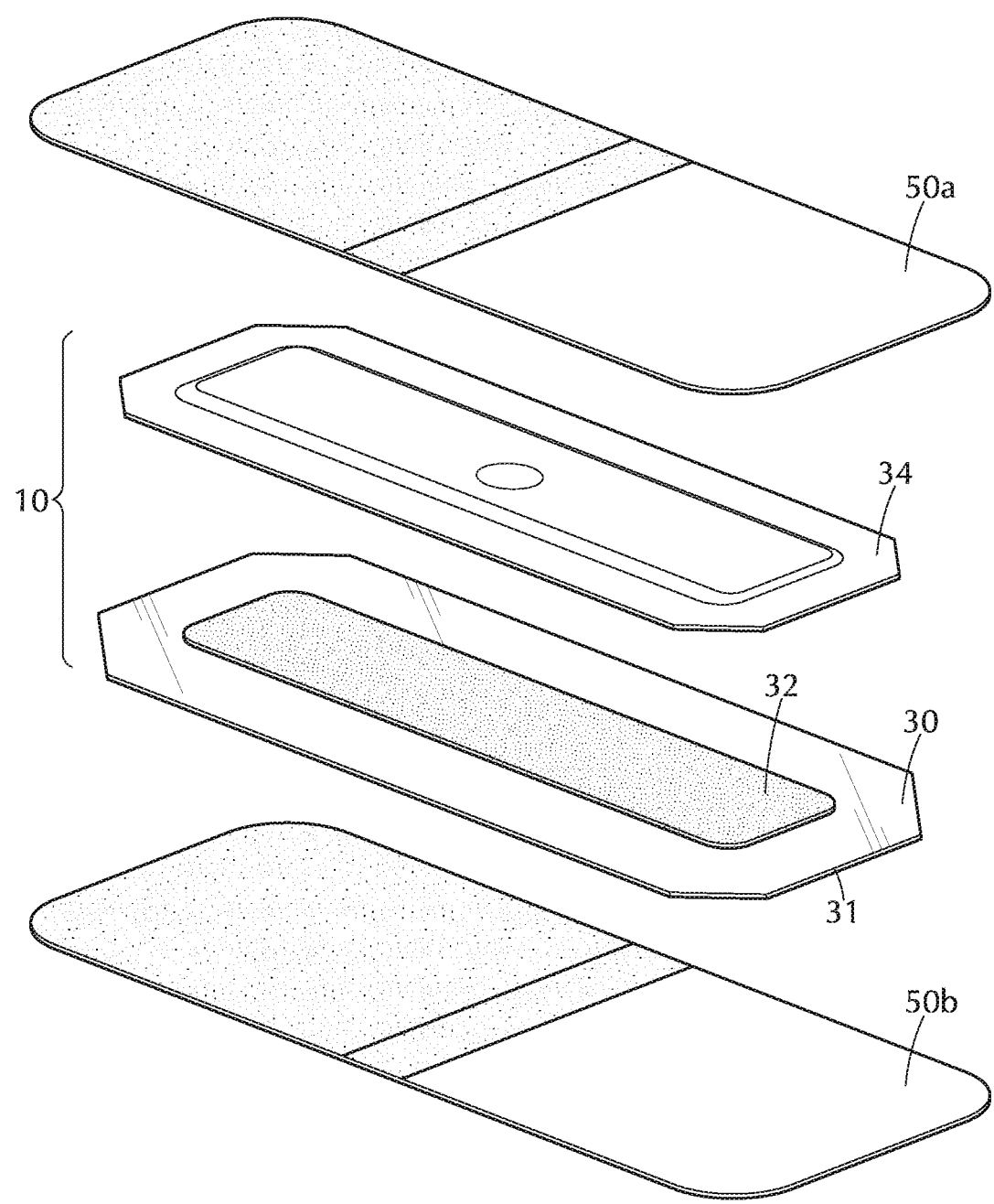
FIG. 15 illustrates an embodiment of an ultrashield between packaging layers in an expanded view.

The ultrashield 10 is packaged so as to reduce or eliminate evaporation of couplant from the couplant layer 32. Thus, such packaging will assist in increasing shelf-life and ensure that the ultrashield 10 is desirably functioning when removed from the packaging for use. In some embodiments, as illustrated in FIG. 15, the ultrashield 10 is disposed between packaging layers 50a, 50b. The packaging layers 50a, 50b are sized and configured to encase the ultrashield 10. In most embodiments, the probe contact layer 30 has an adhesive 31 which adheres the probe contact layer to the packaging layer 50b. In some embodiments, when the packaging layer 50b is removed for use, the same adhesive 31 is then used to adhere the ultrashield 10 to the probe 14. The other packaging layer 50a is adhered to the body surface layer 34 with an adhesive which remains on the packaging layer 50a when the packaging layer 50a is removed. Thus, the body surface layer 34 is free of adhesive when ready for use.

Figure 16:
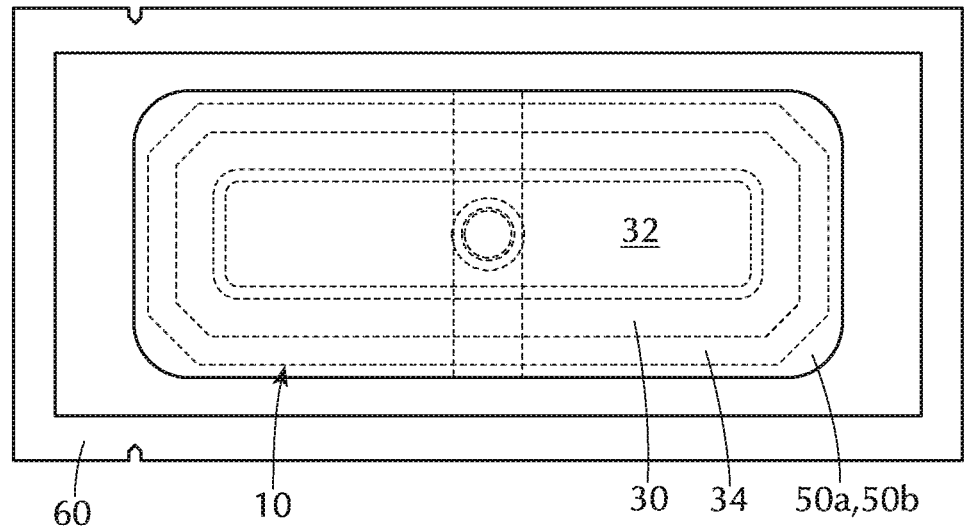
FIG. 16 illustrates an embodiment of an ultrashield in packaging.

FIG. 16 illustrates an embodiment of the ultrashield 10 and packaging in an unexpanded view. Here, the layers 30, 32, 34 are stacked and adhered together to form a single multi-layered ultrashield 10. The ultrashield 10 is held between packaging layers 50a, 50b. And, the packaging layers 50a, 50b are further held within a packaging pouch or sleeve 60. The packaging sleeve 60 protects the packaged ultrashield during transport and storage. The packaging sleeve 60 is comprised of a material, such as aluminum, which reduces water vapor transmission or loss of couplant. In some embodiments, the packaging sleeve 60 allows minimal to no transmission of water vapor or couplant. This ensures the presence of moisture in the ultrashield 10 when the packaging sleeve 60 is opened for use of the ultrashield 10. It may be appreciated that, alternatively or in addition, the packaging layers 50a, 50b may be comprised of a material which reduces water vapor transmission or loss of couplant.

Figure 17:
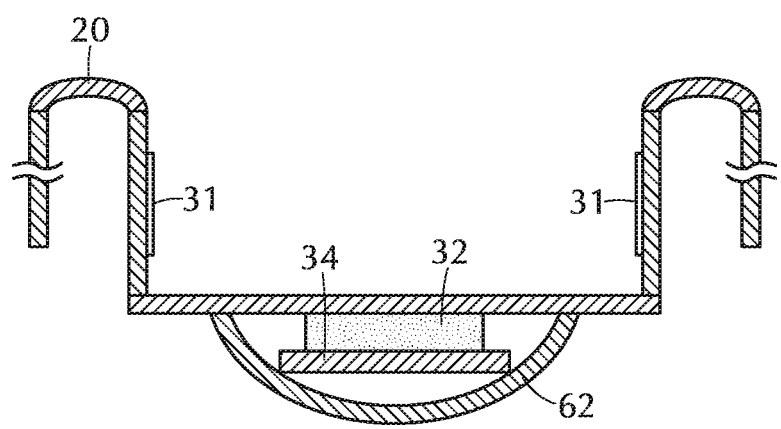
FIG. 17 illustrates an embodiment of an ultrashield which is integral with a probe cover and further comprising a protective pouch.

FIG. 17 illustrates an embodiment of an ultrashield 10 which is integral with a probe cover 20, further comprising a protective pouch 62 which extends over the ultrashield 10 to protect the ultrashield 10 prior to use. In some embodiments, the protective pouch 62 encases the ultrashield 10 so as to resist or prevent water vapor loss or loss of couplant from the couplant layer 32. This provides an extended shelf-life and ensures that the ultrashield 10 is ready for use when the protective pouch 62 is removed from the probe cover 20. Thus, any additional packaging to reduce or eliminate water vapor loss or loss of couplant is not needed and the probe cover 20 may be packaged in a conventional fashion.

Replenishment

As mentioned previously, it may be appreciated that although the body contact layer 34 controls elution of couplant from the couplant layer 32, resisting quick emptying, it is possible for the couplant to eventually empty. This typically occurs during lengthy procedures in which the probe is heavily used. In such instances, the couplant layer 32 may be re-filled with couplant through the body contact layer 34. For example, the body contact layer 34 may be placed into couplant to allow the couplant to absorb through the controlled openings of the layer 34 and into the couplant layer 32 for replenishment.

Figure 18:
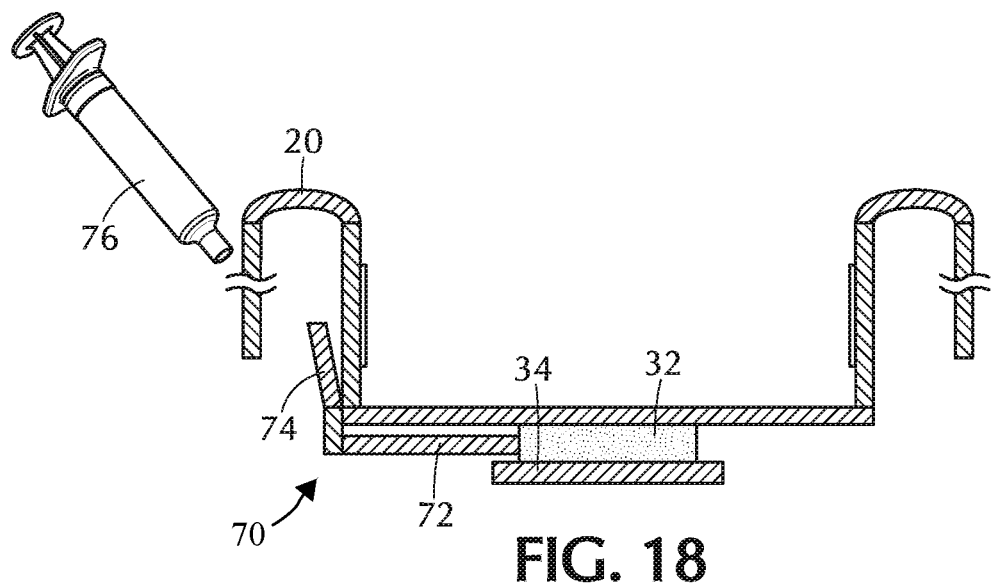
FIGS. 18-19 illustrate an example probe covers having ultrashields and replenishment mechanisms.
Figure 19:
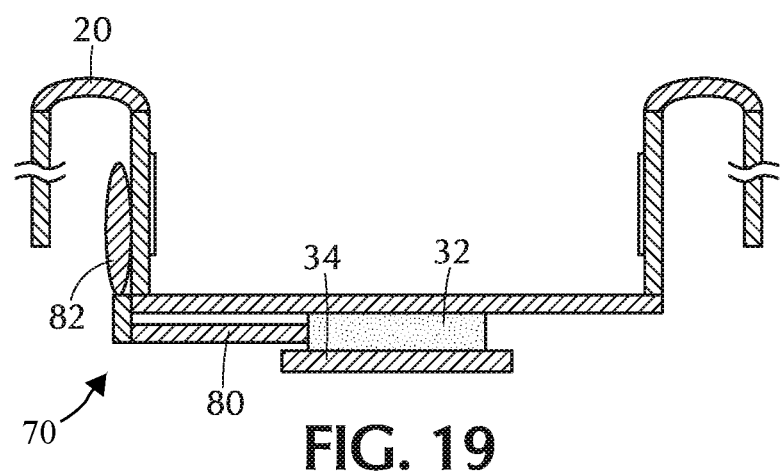

In other embodiments, the couplant layer 32 may be refilled with a replenishment mechanism. FIG. 18 illustrates an example replenishment mechanism 70 comprising a lumen 72 fluidly connected with a fitting 74, such as a luer connection. In this embodiment, the ultrashield 10 is incorporated into a probe cover 20 and the lumen 72 extends along at least a portion of the cover 20 to the couplant layer 32 of the ultrashield 10. Here, the lumen 72 is formed within a tubing or catheter which is affixed to an outside surface the probe cover 20. It may be appreciated that the tubing or catheter having the lumen 72 may alternatively be integral with the probe cover 20. Or the lumen 72 may be formed directly into the probe cover 20. In any case, a device 76 carrying supplemental couplant, such as a syringe, may be attached to the fitting 74 for delivery of the supplemental couplant from the device 76, through the lumen 72 and to the couplant layer 32, as needed. The device 76 may then be removed when not in use. FIG. 19 illustrates another embodiment of a replenishment mechanism 70. In this embodiment, the replenishment mechanism 70 comprises lumen 80 that is prefilled with couplant and is connected with an activation mechanism 82. In this embodiment, the activation mechanism 82 comprises a capsule or flexible pouch that is also pre-filled with couplant. Upon activating the mechanism 82, such as squeezing the capsule, the couplant moves through the lumen 80 to the couplant layer 32. The quantity of delivered couplant is controlled by the activation of the mechanism 82. It may be appreciated that alternatively the lumen 80 may not be prefilled, wherein the lumen 80 receives couplant from the prefilled activation mechanism 82. Likewise, the lumen 80 may be prefilled while the activation mechanism 82 is not prefilled, the activation mechanism 82 causing the couplant in the lumen 80 to be delivered to the couplant layer 32. It may be appreciated that the lumen 80 may be formed within a tubing or catheter which is affixed to an outside surface the probe cover 20. It may be appreciated that the tubing or catheter having the lumen 80 may alternatively be integral with the probe cover 20. Or the lumen 80 may be formed directly into the probe cover 20.

OTHER EMBODIMENTS

Figure 20B:
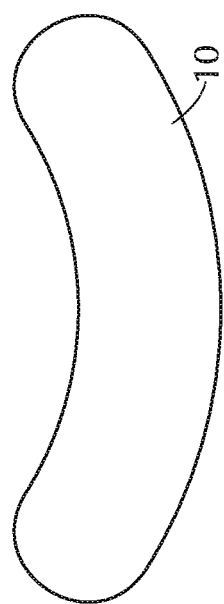
FIGS. 20A-20B illustrate example probe having a curved faceplate and an ultrashield having a corresponding shape.
Figure 20A:
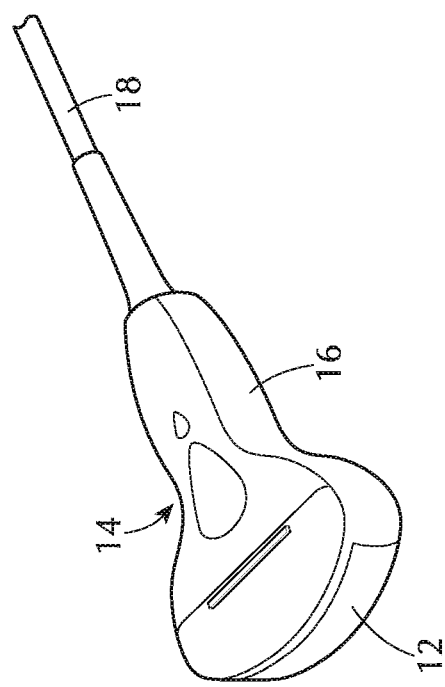
Figure 22B:
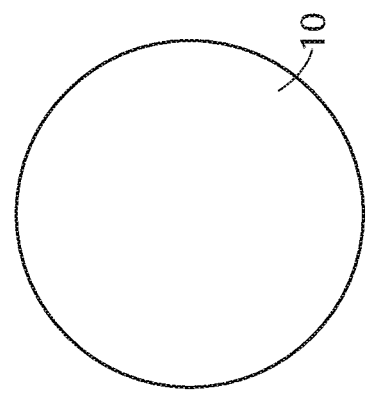
FIGS. 22A-22B illustrate example probe having a round or circular faceplate and an ultrashield having a corresponding shape.
Figure 22A:
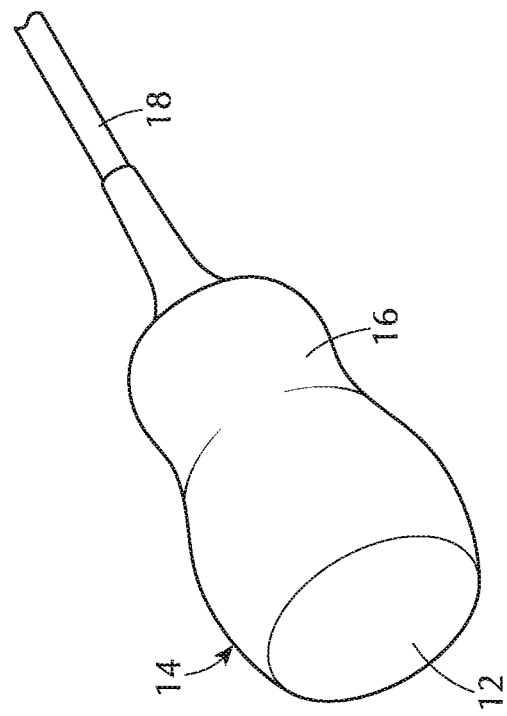
Figure 23B:
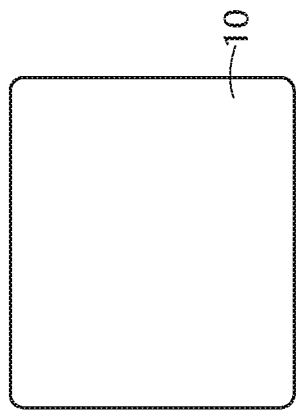
FIGS. 23A-23B illustrate example probe having a square faceplate and an ultrashield having a corresponding shape.
Figure 23A:
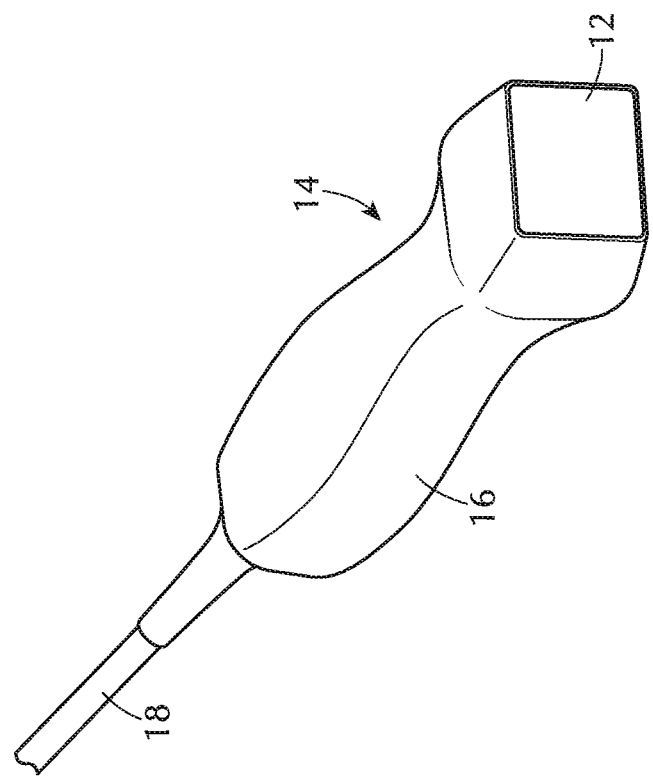
Figure 24A:
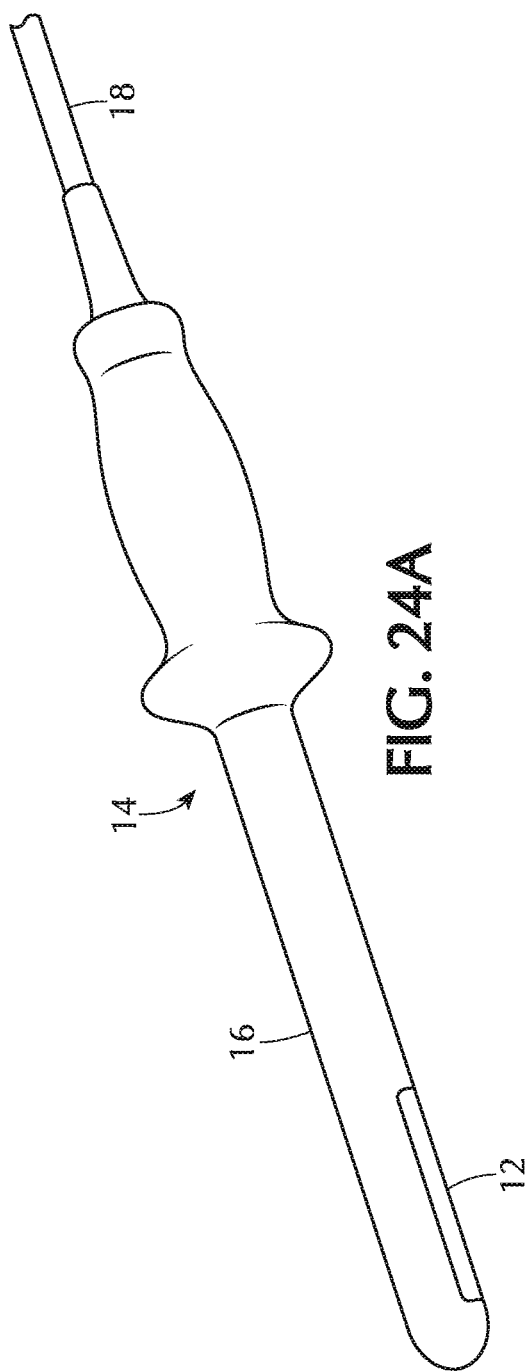
FIGS. 24A-24B illustrate example probe having a rectangular faceplate disposed along a side of an elongate probe housing and an ultrashield having a corresponding shape.
Figure 24B:
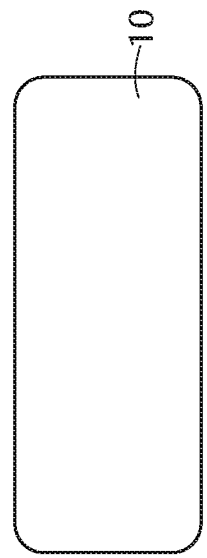

In addition to probes that can be moved across the surface of the body, some probes are designed to be inserted through various openings of the body (e.g. vagina, rectum, esophagus) so that they can get closer to the organ being examined (e.g. uterus, prostate gland, stomach). Getting closer to the organ can allow for more detailed views. Thus, a variety of types of ultrasound probes 14 are available with different shapes and sizes. Likewise, ultrasound probes 14 can have different shapes faceplaces 12, particularly curved faceplates 12. It may be appreciated that ultrashields 10 of the present invention may have various shapes and dimensions to accommodate various types of probes 14. FIG. 20A illustrates an example probe 14 having a curved faceplate 12. FIG. 20B illustrates an embodiment of an ultrashield 10 having a correspondingly curved shape so as to accommodate the curved faceplate 12. Likewise, FIG. 21A illustrates another example probe 14, this one having a smaller curved faceplate 12. FIG. 21B illustrates an embodiment of an ultrashield 10 having a correspondingly curved shape so as to accommodate the curved faceplate 12. FIG. 22A illustrates an example probe having a round or circular faceplate 12. FIG. 22B illustrates an embodiment of an ultrashield 10 having a correspondingly round or circular shape so as to accommodate the faceplate 12. FIG. 23A illustrates an example probe 14 having a square faceplate 12. FIG. 23B illustrates an embodiment of an ultrashield 10 having a correspondingly square shape so as to accommodate the square faceplate 12. FIG. 24A illustrates an example probe 14 having a rectangular faceplate 12 disposed along a side of an elongate probe housing 16. FIG. 24B illustrates an embodiment of an ultrashield 10 having a correspondingly rectangular shape so as to accommodate the rectangular faceplate 12. It may be appreciated that the ultrashields 10 may be shaped to accommodate any style of probe 14. In particular, the couplant layer 32 is sized and configured to cover the faceplate 12 of the probe 14 with which it is to be used and the outside edge of the ultrashield 10 may be sized and configured to desirably adhere to the probe housing 16. Thus, for example, the outside edge of the ultrashield 10 may have a circular shape while the couplant layer 32 within the ultrashield 10 may have a square shape. It may also be appreciated that in some embodiments, the outside edge of the ultrashield 10 may be trimmed at the time of use to desirably conform and adhere to the probe housing 16.

It may be appreciated that in some embodiments, the body is a human body and in other instances the body is the body of an animal or object.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device comprising:
   a couplant layer comprising a couplant material comprising a hydrogel configured to retain water in a colloidal condition and configured to be formed into a self-standing sheet, the couplant layer having a couplant flowable from the couplant material, wherein the couplant comprises the water; and
   at least one external layer having a plurality of openings and coupled to the couplant layer, at least one of the at least one external layer comprising an adhesive, wherein the couplant layer and the at least one external layer are flexible and configured to allow ultrasound wave transmission through a surface while transmitting ultrasound from an ultrasound probe, one of the at least one external layer comprising an outer surface body contact layer that is plasma treated or coated with a fine film of biocompatible material to reduce friction.

2. The device of claim 1, wherein the couplant layer comprises a rectangular shape approximately 2.5 inches long and 0.5 inches wide.

3. The device of claim 1, wherein the outer surface body contact layer curves as to attach to the ultrasound probe.

4. The device of claim 1, wherein the outer surface body contact layer is configured to control an amount and rate of couplant dispensed.

5. The device of claim 1, wherein the outer surface body contact layer is configured to be placed into the couplant and configured to allow the couplant to absorb through the plurality of openings.

6. The device of claim 1, wherein the plurality of openings comprise openings that all have a uniform size.

7. The device of claim 1, wherein each of the openings has a size from 0.2 to 2.0 microns.

8. The device of claim 1, wherein each of the openings has a size from 0.5 to 5 microns.

9. The device of claim 1, wherein each of the openings is a 1 micron opening.

10. The device of claim 1, wherein each of the openings is a 2 micron opening.

11. The device of claim 1, wherein each of the openings is a 3 micron opening.

12. The device of claim 1, wherein each of the openings is a 4 micron opening.

13. The device of claim 1, wherein each of the openings is a 10 micron opening.

14. The device of claim 1, wherein each of the openings has a size from 0 to 10 microns.

15. The device of claim 1, wherein the at least one external layer comprises a stretchable surface.

16. A system, comprising:
    a first layer comprising a couplant material comprising a hydrogel configured to retain water in a colloidal condition and configured to be formed into a self-standing sheet, the first layer having a couplant flowable from the couplant material, wherein the couplant comprises the water; and
    at least one second layer having a plurality of openings and coupled to the first layer, at least one of the at least one second layer comprising an adhesive, wherein the first layer and the at least one second layer are flexible and configured to allow ultrasound wave transmission through a surface while transmitting ultrasound from an ultrasound probe, one of the at least one second layer comprising an outer surface body contact layer that is plasma treated or coated with a fine film of biocompatible material to reduce friction.

17. The system of claim 16, further comprising a third layer coupled to the first layer that connects with the ultrasound probe and comprises a flexible film.

18. The system of claim 17, wherein the third layer comprises an adhesive on one side of the third layer that adheres to the ultrasound probe.

19. The system of claim 18, further comprising a first packaging layer and a second packaging layer held within a packaging pouch that holds the first layer, the at least one second layer, and the third layer therein.

* * * * *